United States Patent [19]

Dunlop

[11] 4,219,486
[45] Aug. 26, 1980

[54] N,N-BIS(5-HYDROXYMETHYLFURFURYL)-METHYLAMINE AND PROCESS OF PREPARATION

[75] Inventor: Andrew P. Dunlop, Riverside, Ill.

[73] Assignee: The Quaker Oats Company, Chicago, Ill.

[21] Appl. No.: 62,368

[22] Filed: Jul. 31, 1979

[51] Int. Cl.$^2$ .......................................... C07D 307/52
[52] U.S. Cl. .................................. 260/347.7; 528/73
[58] Field of Search ...................................... 260/347.7

[56] References Cited

U.S. PATENT DOCUMENTS

| | | | |
|---|---|---|---|
| 2,995,582 | 8/1961 | Garber et al. | 260/347.7 |
| 4,124,604 | 11/1978 | Yu | 260/347.7 |
| 4,162,327 | 7/1979 | Knoll | 260/347.7 X |

Primary Examiner—Richard Raymond
Attorney, Agent, or Firm—Neuman, Williams, Anderson & Olson

[57] ABSTRACT

The new composition of matter, N,N-bis(5-hydroxymethylfurfuryl)methylamine.

2 Claims, No Drawings

N,N-BIS(5-HYDROXYMETHYLFURFURYL)METHYLAMINE AND PROCESS OF PREPARATION

This invention relates to a new composition of matter.

The new composition of matter of this invention is N,N-bis(5-hydroxymethylfurfuryl)methylamine having the formula:

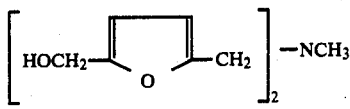

The above new composition of matter is readily produced in substantially quantitative yields at relatively low temperatures by admixing 1.5 moles of methyl amine with 3 moles of formaldehyde in aqueous acid solution and adding thereto furfuryl alcohol (3 moles). The reaction is exothermic in nature and the reaction is conducted without deliberate heating. The resulting solution contains the product N,N-bis(5-hydroxymethylfurfuryl)methylamine which precipitates from solution upon neutralization with a base such as sodium hydroxide.

The following example illustrates a preferred synthesis of the new composition of matter.

EXAMPLE 243.2 grams (3 moles) of formalin (37% aqueous solution of formaldehyde), 116.3 grams (1.5 moles) of a 40% aqueous solution of methyl amine and 140 grams of concentrated hydrochloric acid (1.42 moles) were mixed with cooling. Then 294.0 grams of furfuryl alcohol (3.0 moles) is added dropwise over a period of approximately ½ hour. The temperature of the resulting mixture rises exothermically to about 60° C. After addition of all of the furfuryl alcohol the mixture is stirred an additional 2 to 2½ hours while being maintained at a temperature of approximately 60° C. Upon neutralization with an excess of sodium hydroxide the desired product N,N-bis(5-hydroxymethylfurfuryl)methylamine precipitates.

To remove any sodium chloride salt which is formed by neutralization an 80/20 volume percent solution of methyl chloride and methanol is added to the precipitated product causing it to dissolve. The mixture is then transferred to a separatory funnel and shaken to cause formation of two liquid layers. The desired product is in the methyl chloride layer and sodium chloride in the aqueous methanol layer, which are separated. The aqueous methanol layer is extracted again with an 80/20 solution of methyl chloride and methanol with the combined methyl chloride layers being dried over magnesium sulfate and sodium carbonate. The methyl chloride solvent is then stripped from the product.

The product isolated by preparative scale gel permeation chromatography using tetrahydrofuran as solvent was subjected to infrared (IR) and nuclear magnetic resonance (NMR) analyses which confirmed its structure. The proton (acetone-$d_6$) NMR analysis of the compound shows single peaks at $\delta 2.22$, $\delta 3.57$, $\delta 4.53$, $\delta 6.25$ and $\delta 3.4$ (variable) ppm. These peaks correspond to the $CH_3$-H, N-$CH_2$-furan, furan-H, furan-$CH_2$-O-, and O-H proton resonances, respectively.

The infrared spectrum contained a very broad OH stretch band centered at 3350 cm$^{-1}$, weak furan ring CH stretch vibrations at 3120 cm$^{-1}$, strong $CH_2$ and $CH_3$ stretch vibrations at 2790–2950 cm$^{-1}$, medium furan ring C=C stretch at 1565 cm$^{-1}$ and 1415–1470 cm$^{-1}$, strong ether CO stretch band at 1012 cm$^{-1}$, and a strong HC=CH wag vibration at 795 cm$^{-1}$.

Following the procedure in the above example, additional syntheses were carried out at various pH values by using an amount of hydrochloric acid to give various pH levels. These syntheses at various pH levels are summarized as follows:

| Synthesis | pH | % Yield of Product |
|---|---|---|
| A | 1.0 | 92 |
| B | 3.3 | 74 |
| C | 4.0 | 20 |
| D | 1.0 | 94 |
| E | 1.0 | 84 |
| F | 1.0 | 93 |
| G | 1.0 | 94 |

The N,N-bis(5-hydroxymethylfurfuryl)methylamine composition of the present invention is useful in the fabrication of polyurethane compositions containing a substantial furan ring-portion thereof. Reaction of the composition of the present invention with a polyisocyanate results in the formation of a polyurethane. The composition of the invention provides not only a diol for reaction with the polyisocyanate, but also provides a tertiary amine catalyst component which becomes incorporated into the resulting urethane polymer structure.

Those modifications and equivalents which fall within the spirit of the invention are to be considered a part thereof.

What is claimed is:

1. As a new composition of matter, N,N-bis(5-hydroxymethylfurfuryl)methylamine.

2. A process for preparing N,N-bis(5-hydroxymethylfurfuryl)methylamine which comprises admixing methylamine with formaldehyde in aqueous acid solution and adding to the mixture furfuryl alcohol.

* * * * *